US012136284B2

(12) United States Patent
Robles et al.

(10) Patent No.: US 12,136,284 B2
(45) Date of Patent: Nov. 5, 2024

(54) LABEL-FREE HEMATOLOGY AND PATHOLOGY ANALYSIS USING DEEP-ULTRAVIOLET MICROSCOPY

(71) Applicant: Georgia Tech Research Corporation, Atlanta, GA (US)

(72) Inventors: Francisco E. Robles, Atlanta, GA (US); Ashkan Ojaghi, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 359 days.

(21) Appl. No.: 17/767,328

(22) PCT Filed: Oct. 13, 2020

(86) PCT No.: PCT/US2020/055431
§ 371 (c)(1),
(2) Date: Apr. 7, 2022

(87) PCT Pub. No.: WO2021/072408
PCT Pub. Date: Apr. 15, 2021

(65) Prior Publication Data
US 2022/0366709 A1 Nov. 17, 2022

Related U.S. Application Data

(60) Provisional application No. 62/915,495, filed on Oct. 15, 2019, provisional application No. 62/913,611, filed on Oct. 10, 2019.

(51) Int. Cl.
*G06V 20/69* (2022.01)
*G01N 21/33* (2006.01)
(Continued)

(52) U.S. Cl.
CPC .......... *G06V 20/698* (2022.01); *G01N 21/33* (2013.01); *G01N 33/49* (2013.01); *G02B 21/16* (2013.01);
(Continued)

(58) Field of Classification Search
CPC .... G06V 20/698; G06V 10/70; G06V 20/693; G06V 20/695; G06V 10/143;
(Continued)

(56) References Cited

U.S. PATENT DOCUMENTS 5,991,028 A 11/1999 Cabib et al.
11,592,652 B2 * 2/2023 Wang ................. G01N 29/2425
(Continued)

FOREIGN PATENT DOCUMENTS

CN 1338970 A 3/2002
CN 107109340 A 8/2017
(Continued)

OTHER PUBLICATIONS

International Search Report and Written Opinion from Application No. PCT/US2020/055431 dated Jan. 28, 2021.
(Continued)

*Primary Examiner* — Diane D Mizrahi
(74) *Attorney, Agent, or Firm* — Troutman Pepper Hamilton Sanders LLP; Ryan A. Schneider; Korbin M. Blunck

(57) ABSTRACT

A deep-ultraviolet microscopy system includes a light source for outputting a light beam for illuminating a biological sample, the light beam being inclusive of ultraviolet wavelengths; a reception space for reception of a biological sample for illumination by the light beam; an ultraviolet microscope objective for collecting and relaying light that interacts with the biological sample to an image capture device; and an ultraviolet sensitive image capture device for
(Continued)

capturing images of the biological sample, with the microscopy system configured to capture multiple images of the biological sample at one or more ultraviolet wavelengths. A method of processing ultraviolet images of biological samples includes receiving a plurality of multi-spectral ultraviolet images of a biological sample; normalizing and scaling the images; and assigning each image to a channel in the RGB color-space based on wavelength.

16 Claims, 12 Drawing Sheets

(51) Int. Cl.
| | | |
|---|---|---|
| *G01N 33/49* | (2006.01) | |
| *G02B 21/16* | (2006.01) | |
| *G02B 21/36* | (2006.01) | |
| *G06T 3/40* | (2024.01) | |
| *G06V 10/70* | (2022.01) | |
| *H04N 9/64* | (2023.01) | |
| *H04N 23/56* | (2023.01) | |

(52) U.S. Cl.
CPC .............. *G02B 21/365* (2013.01); *G06T 3/40* (2013.01); *G06V 10/70* (2022.01); *G06V 20/693* (2022.01); *G06V 20/695* (2022.01); *H04N 9/64* (2013.01); *H04N 23/56* (2023.01); *G01N 2201/0621* (2013.01)

(58) Field of Classification Search
CPC .................. G01N 21/33; G01N 33/49; G01N 2201/0621; G01N 2015/1006; G01N 2015/1472; G01N 2015/1488; G01N 2201/0627; G02B 21/16; G02B 21/365; G02B 27/0025; G06T 3/40; G06T 2207/10056; G06T 7/0012; G06T 2207/30024; H04N 9/64; H04N 23/56; H04N 23/84; G16H 50/20; G16H 30/40
See application file for complete search history.

(56) References Cited

U.S. PATENT DOCUMENTS

| | | |
|---|---|---|
| 2001/0033364 A1 | 10/2001 | Cabib |
| 2005/0074745 A1 | 4/2005 | Clayton et al. |
| 2005/0280906 A1 | 12/2005 | Scheiner et al. |
| 2009/0208072 A1 | 8/2009 | Seibel et al. |
| 2010/0098742 A1 | 4/2010 | Vacanti et al. |
| 2010/0181288 A1 | 7/2010 | Tang et al. |
| 2011/0228072 A1 | 9/2011 | Van Leeuwen et al. |
| 2012/0145926 A1 | 6/2012 | Seibel et al. |
| 2014/0315295 A1 | 10/2014 | Makarova et al. |
| 2015/0268244 A1 | 9/2015 | Cho et al. |
| 2016/0350914 A1 | 12/2016 | Champlin et al. |

FOREIGN PATENT DOCUMENTS

| | | |
|---|---|---|
| EP | 2270712 A1 | 1/2011 |
| JP | 2011512543 A | 4/2011 |
| JP | 2012510069 A | 4/2012 |

OTHER PUBLICATIONS

European Search Report from Application No. 20874587.7 dated Sep. 10, 2023.
Ojaghi, et al., "Label-Free Identification of Neutropenia Using Deep-Ultraviolet Microscopy," Progress in Biomedical Optics and Imaging, SPIE—International Society for Optical Engineering Feb. 20, 2019 vol. 10885.
Ojaghi, et al., "Label-free Hematology Analysis Using Deep-Ultraviolet Microscopy," Proceedings of the National Academy of Sciences Jun. 20, 2020, vol. 117, No. 26.
Ojaghi, et al., "Deep-Ultraviolet Microscopy for Label-Free Hematological Analysis," Progress in Biomedical Optics and Imaging—SPIE International Society for Optical Engineering Feb. 14, 2020, vol. 11247.
Office Action from Chinese Application No. 202080052163.8 dated Jul. 19, 2024.
Office Action from Japanese Application No. 2022-521445 dated Jun. 6, 2024.

\* cited by examiner c

A

LABEL-FREE HEMATOLOGY AND PATHOLOGY ANALYSIS USING DEEP-ULTRAVIOLET MICROSCOPY

ACKNOWLEDGEMENT OF GOVERNMENT SUPPORT

The present inventions were made with government support under Award No. 1752011, awarded by the National Science Foundation. The government has certain rights in the inventions set forth herein.

FIELD OF THE INVENTION

The present invention relates to an apparatus and method for hematological and histopathological analysis of biological samples. In particular, the present invention is directed to systems and methods for label-free hematology and histopathology assessments of live and fixed cells and tissues using deep-ultraviolet microscopy.

BACKGROUND OF THE INVENTION

Hematological analysis of blood cells has been the standard method for routine clinical diagnosis and monitoring of many blood diseases such as sickle cell anemia, neutropenia, and thrombocytopenia. Current hematological practices rely on assessing alterations in morphology, population, and molecular or cytogenetic properties of blood cells to diagnose diseases. In these practices, peripheral blood is collected and analyzed using a hematology analyzer to obtain a complete blood count (CBC). Modern hematology analyzers use a combination of multiple techniques such as absorption spectroscopy, impedance measurement, and flow cytometry to measure red blood cell (RBC) and platelet counts as well as white blood cell (WBC) differentials[1] (i.e., neutrophil, eosinophil, basophil, lymphocyte, and monocyte counts). Although hematology analyzers are capable of automated and rapid staining and analysis of several samples[2], they are costly and require multiple reagents and intensive maintenance.

CBC is one of the most common medical tests[3], often performed by trained technicians at healthcare centers, necessitating patients to make several trips for routine tests which further adds to the cost and labor of these tests and limits monitoring frequency for patients with severe conditions. In addition, for abnormal and pathological samples that produce atypical results, manual microscopic examination is often required to confirm CBC results[1]. Microscopic analysis of peripheral blood is performed by fixing and staining the smear samples using Romanowsky-type stains which are generally composed of a blue dye (e.g., methylene blue) and an acidic dye (e.g., eosin), resulting in pink erythrocytes and leukocytes with violet nuclei and dark blue cytoplasm containing red-purple granules[1]. Accurate evaluation of peripheral blood smears requires well-stained samples and time-consuming microscopic analysis performed by trained personnel and is prone to staining variability.

Alternative techniques such as fluoresce labeling have also been used extensively both for visual assessment[4,5] and flow cytometry[6-8] of blood cells, however the chemical staining procedures or genetic modifications associated with this method are invasive and suffer from drawbacks such as phototoxicity and photobleaching[9]. To address this issue, several label-free modalities have been developed based on various endogenous signatures such as confocal laser scanning microscopy (CLSM)[10,11], spectrally encoded detection[12], photothermal imaging[13], Raman microscopy[14], hyperspectral imaging[15], fluorescence lifetime imaging microscopy (FLIM)[16], two photon autofluorescence[17-19], third harmonic generation[20], and quantitative phase imaging[9,21-23]. Although these methods reveal structural and biochemical signatures that can be used for cellular phenotyping and differentiation, the need for careful calibration, complexity of the optical setups, and high equipment costs preclude their use in clinical and point-of-care settings. Recently, technologies working based on optical imaging of microcirculation in capillaries have enabled point-of-care WBC detection, however such methods are not able to fully differentiate and visualize all WBC subtypes which limits their application to diseases such as neutropenia.

Despite the advances provided to date in the art, there remains no label-free technology suitable for point-of-care settings that can achieve high quality visualization and accurate quantitative differentiation of all blood cell types.

SUMMARY OF THE INVENTION

A deep-ultraviolet microscopy system according to the present invention comprises a light source for outputting a light beam for illuminating a biological sample, the light beam output from the light source comprising ultraviolet wavelengths; a reception space for reception of a biological sample for illumination by the light beam output from the light source; an ultraviolet microscope objective for collecting light that has interacted with the biological sample and for relaying the collected light to an image capture device; and an ultraviolet sensitive image capture device for capturing images of the light that is relayed from the ultraviolet microscope objective. The ultraviolet microscope objective is adapted to collect light that has interacted with the biological sample, which may include absorption and scattering in transmission or back-reflection; and the image capture device is a UV sensitive camera configured to capture multiple images of the biological sample at one or more ultraviolet wavelengths.

In one example, the light source may be a broadband light source configured for outputting a light beam comprising ultraviolet wavelengths and non-ultraviolet wavelengths; and the system may further comprise one or more band-pass filters positioned downstream from the light source for filtering the light beam output from the light source to remove non-ultraviolet wavelengths and to relay ultraviolet wavelengths. The system may comprise one or more band-pass filters, with the band-pass filters supported on a filter stage that is configured for switching between the two or more band-pass filters, such as a filer wheel. The band-pass filters may include one or more band-pass filters for passing light in a narrow band ultraviolet wavelength centered around a wavelength in a range of 200-450 nm, where a narrow band comprises bandwidths of 50 nm or less.

A short-pass dichroic mirror may be provided for filtering out non-ultraviolet wavelengths from the light beam output from the light source, the short-pass dichroic mirror being positioned between the light source and the one or more band-pass filters. A parabolic mirror may also be provided for removing chromatic aberrations and converging the light beam that is output from the light source, the parabolic mirror being positioned between the light source and the one or more band-pass filters and upstream from the short-pass dichroic mirror.

In another example, the light source may be one or more LEDs, each LED being configured to output light consisting of narrow band ultraviolet wavelengths, where a narrow band comprises bandwidths of 50 nm or less. The light source may be two or more, or at least three LEDs, with each LED configured to output ultraviolet wavelengths that differ from ultraviolet wavelengths of the other LED(s). One or more of the LEDs may be configured for passing light in a narrow band ultraviolet wavelength centered around a wavelength in a range of 200-450 nm.

In use, deep-ultraviolet microscopy systems according to the present invention may be used for imaging biological samples, which may include biological samples chosen from: a blood sample; a bone marrow sample; and a tissue sample. The biological samples may be live samples or fixed samples. A single biological sample may comprise two or more different biological components, such as a blood sample that comprises different biological components in the form of: red blood cells, white blood cells, and platelets.

Images created with deep-ultraviolet microscopy systems according to the present invention may be used in hematology or histopathology of the imaged biological sample. The images may be used for identifying and phenotyping unique types of cells, and for phenotyping and diagnosing of blood, bone marrow, and tissues samples.

The present invention is also inclusive of a colorization scheme in which a plurality of ultraviolet images of a biological sample are received, including images captured at one, two or three or more ultraviolet wavelengths; with each image then being transformed into a colored image. The ultraviolet images may be received from a physical storage medium or in an electronic signal transmitted from an image capture device. Prior to transforming each ultraviolet image, each image may be normalized by a blank image captured at a corresponding wavelength and then scaled with a weight factor and gamma factor that are chosen based on the wavelength of the given ultraviolet image.

Transforming the ultraviolet images to a colored image comprises assigning each scaled ultraviolet image to a channel in the RGB color-space based on the wavelength of the scaled ultraviolet image, with each scaled ultraviolet image to assigned a channel in the RGB color-space based on the wavelength of the scaled ultraviolet image. Assignment of the ultraviolet may comprise assigning ultraviolet images of a first wavelength to a red channel, assigning ultraviolet images of a second wavelength to a green channel, and assigning ultraviolet images of a third wavelength to a blue channel. In another example, images acquired at one or more ultraviolet wavelengths may be combined using a dimensionality reduction technique, such as principle component analysis of phasor analysis, to transform the ultraviolet images to a colored image. The ultraviolet images may be colored to mimic colors of medical stains such as: hematoxylin and eosin stain; Giemsa stain; and immunohistochemistry stains; and any coloring selected to distinguish molecular and structural entities in the image.

Both the foregoing general description and the following detailed description are exemplary and explanatory only and are intended to provide further explanation of the invention as claimed. The accompanying drawings are included to provide a further understanding of the invention; are incorporated in and constitute part of this specification; illustrate embodiments of the invention; and, together with the description, serve to explain the principles of the invention.

BRIEF DESCRIPTION OF THE DRAWINGS

Further features and advantages of the invention can be ascertained from the following detailed description that is provided in connection with the drawings described below.

DETAILED DESCRIPTION OF THE INVENTION

Figure 1:
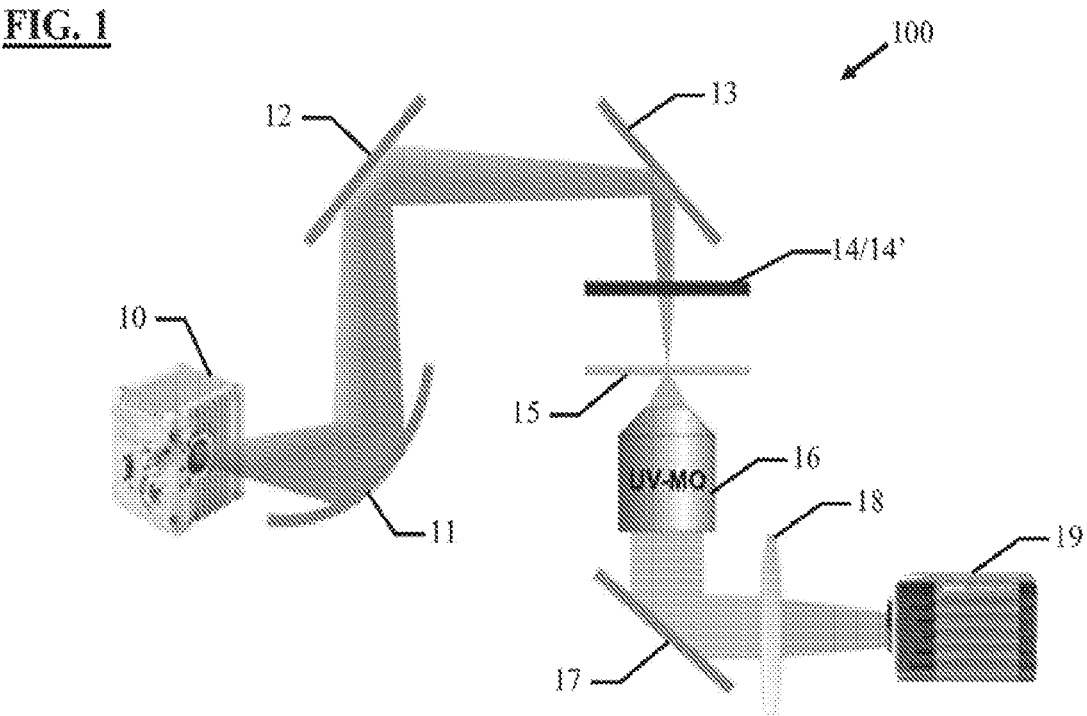
FIG. 1 shows an ultraviolet microscopic system according to the present invention.

The following disclosure discusses the present invention with reference to the examples shown in the accompanying drawings, though does not limit the invention to those examples.

The use of any and all examples, or exemplary language (e.g., "such as") provided herein is intended merely to better illuminate the invention and does not pose a limitation on the scope of the invention unless otherwise claimed. No language in the specification should be construed as indicating any non-claimed element as essential or otherwise critical to the practice of the invention, unless made otherwise clear in context.

As used herein, the singular forms "a," "an," and "the" include plural referents unless the context clearly dictates otherwise. Unless indicated otherwise by context, the term "or" is to be understood as an inclusive "or." Terms such as "first", "second", "third", etc. when used to describe multiple devices or elements, are so used only to convey the relative actions, positioning and/or functions of the separate devices, and do not necessitate either a specific order for such devices or elements, or any specific quantity or ranking of such devices or elements.

The word "substantially", as used herein with respect to any property or circumstance, refers to a degree of deviation that is sufficiently small so as to not appreciably detract from the identified property or circumstance. The exact degree of deviation allowable in a given circumstance will depend on the specific context, as would be understood by one having ordinary skill in the art.

Use of the terms "about" or "approximately" are intended to describe values above and/or below a stated value or range, as would be understood by one having ordinary skill in the art in the respective context. In some instances, this may encompass values in a range of approx. +/−10%; in other instances there may be encompassed values in a range of approx. +/−5%; in yet other instances values in a range of approx. +/−2% may be encompassed; and in yet further instances, this may encompass values in a range of approx. +/−1%.

It will be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless indicated herein or otherwise clearly contradicted by context.

Recitations of a value range herein, unless indicated otherwise, serves as a shorthand for referring individually to each separate value falling within the stated range, including the endpoints of the range, each separate value within the range, and all intermediate ranges subsumed by the overall range, with each incorporated into the specification as if individually recited herein.

Unless indicated otherwise, or clearly contradicted by context, methods described herein can be performed with the individual steps executed in any suitable order, including: the precise order disclosed, without any intermediate steps or with one or more further steps interposed between the disclosed steps; with the disclosed steps performed in an order other than the exact order disclosed; with one or more steps performed simultaneously; and with one or more disclosed steps omitted.

Deep ultraviolet (UV) light (i.e., 200-400 nm) for microscopy is a promising new tool for quantitative structural and biochemical analysis of biological samples[24]. Deep-UV microscopy offers many potential advantages over traditional methods, such as higher spatial resolution due to the shorter wavelength of UV light, and the ability to access information from many endogenous biomolecules that play an important role in cell structure and function[25,26]. Label-free imaging of live cells has been achieved using microscopy systems working in the deep-UV wavelength range over extended periods of time (~6 hours) without inducing apoptosis[24,27]. In addition, cell phenotyping and identification can be realized using the information-rich UV images from which key intracellular architectural[24,28-30] and biochemical features can be extracted.

Aspects of the present invention are inclusive of label-free assessment of live blood cells based on deep-UV microscopy. These assessments provide quantitative endogenous molecular information from live cells and enable analysis and differentiation of blood cell types based on their molecular and structural signatures. Systems and methods according to the present invention have proven successful in achieving a quantitative five-part differential WBC classification, with clear visualization of platelets, and normal and sickled RBCs. The present invention is further inclusive of a pseudo-colorization scheme that accurately mimics the colors produced by standard Giemsa staining, and enable visual examination of blood smears through use of wide-field pseudo-colored UV images that may serve as a substitute to conventional bright-field microscopy imaging practices.

Thus, there is provided a low-cost, portable hematology analyzer that circumvents the limitations of conventional systems, and which enable fast and easy in-home or clinical testing that parallels those otherwise available through existing conventional technologies.

FIG. 1 shows one example of a deep-UV multi-spectral microscopy system 100 according to the present invention. The system 100 includes a light source 10 (e.g., an ultra-broadband plasma source); a parabolic mirror 11; a short-pass dichroic mirror 12; a first mirror 13; a UV filter wheel 14 having a number of UV band-pass filters 14'; a biological sample 15 (e.g., blood smear sample; a pathology tissue; bone marrow, etc.); a UV microscope objective (UV-MO) 16; a second mirror 17; a tube lens 18; and a UV-sensitive camera 19.

The system 100 is configured to provide images from live unstained cells in the biological sample 15, at different wavelengths in the 200-450 nm range, with deep-UV band-pass filters 14' that are adapted for tuning the imaging wavelength to absorption peaks of major biochemical components in cells of the sample 15. For example, in the study of human cells, the band-pass filters 14' may be tuned for nucleic acids having an absorption peak at 260 nm and for proteins having an absorption peak at 280 nm[24,28]. With the foregoing configuration, the system 100 is adapted for generating multi-spectral images that are rich with information as to the structural and biochemical properties of cells.

In one non-limiting working example of the deep-UV microscopy system 100, the plasma source 10 was provided in the form of an incoherent broadband laser-driven plasma light source (EQ-99X LDLS, Energetiq Technology). The output light from the broadband plasma source 10 was collected through an off-axis parabolic mirror 11 (Newport Corporation) and relayed to the position of the sample 15 using a short-pass dichroic mirror 12 (Thorlabs, NJ, USA). This system 100 performed multi-spectral imaging using UV band-pass filters 14' (Chroma Technology Corp, VT, USA) installed on a filter wheel 14, allowing switching between the band-pass filters 14' for acquisition of images at three wavelength regions centered at 260 nm, 280 nm, and 300 nm. The system 100 was measured at the sample plane as generating light intensities of 0.37 Mw at 260 nm, 1.75 mW at 280 nm, and 0.22 mW at 300 nm. For imaging, a 40× UV microscope objective (NA 0.5) (LMU-40X, Thorlabs), was used to achieve an average spatial resolution of approximately 280 nm. A UV sensitive CCD camera (pco.ultraviolet, PCO AG, Kelheim, Germany), with an integration time=30-100 ms, was used for recording images of the samples. A three-axis high-precision motorized stage (MLS2031, Thorlabs) was used for translating and adjusting the samples for focusing during imaging.

Prior to imaging, the whole blood samples were collected from healthy donors and added to an anticoagulant solution (sodium citrate, Beckton Dickenson) according to approved protocols by Institutional Review Boards of Georgia Institute of Technology and Emory University. Blood smears were then made on un-coated quartz slides by using 10 μL of whole blood, and the samples were then dried in air for 5 minutes before UV imaging was performed without any cell fixation or staining. Images were then recorded while each sample was translated and adjusted for focusing via the three-axis high-precision motorized stage. By raster scanning the sample, a series of UV images from a 1×2 mm area were acquired at each wavelength in approximately 3 minutes.

After imaging with the deep-UV microscopy setup, comparative Giemsa stained bright-field images were obtained by fixing and staining the samples, and imaging the stained samples using an upright microscope (Axioskop 2 Plus, Carl Zeiss, Germany) equipped with a 40× objective (numerical aperture (NA) 0.6). These samples were first fixed using methanol (Thermo-scientific) for 7 minutes and stained in May-Grünwald solution (MG500, Sigma Aldrich Inc., USA) for 15 minutes. After a brief rinse, samples were put in a 1:10 diluted Giemsa stain solution (GS500, Sigma Aldrich Inc., USA) for 20 minutes, and were then washed in a phosphate buffer solution (PBS) having a pH 6.6 and air-dried for bright field microscopy. By scanning the sample, a series of images from the 1×2 mm area on the sample was acquired. The tile scan images were then normalized using an image acquired from a blank region on the sample and stitched using the Zeiss Zen Black edition software (Carl Zeiss, Germany) to obtain a wide-field image.

Additional images were obtained from samples containing the less abundant polymorphonuclear leukocytes (PMNLs)—i.e., neutrophils, basophils, and eosinophils—isolated from the whole blood. These additional images were obtained through a magnetic antibody-based selection technique in which live human PMNLs were isolated via negative magnetic antibody-based selection with the MACSxpress isolation kit (Miltenyi Biotec) and re-suspended in RPMI media with L-glutamine and HEPES (Life Technologies). In order to induce and maintain a normal cell spreading[34] and adhesion to the microscope slide surface, quartz slides were coated with a 1 nM solution of N-Formylmethionine-leucyl-phenylalanine (fMLP, Sigma-Aldrich Inc., USA) for 60 minutes, then rinsed with distilled water and phosphate buffer saline (PBS). The cell suspension was pipetted onto the coated slide and incubated for another 30 minutes. Slides were then washed with distilled water and dried before imaging.

The acquired multi-spectral images were then processed and utilized in a pseudo-colorization scheme as well as machine learning-based WBC differential. After obtaining the tile image series at the three wavelengths, each image was normalized by a reference background image acquired from a blank area on the sample at each wavelength to remove any illumination artifacts. Then, to obtain accurate colorization of UV images, an intensity-based image registration algorithm (based on imregister function), implemented in MATLAB (MathWorks), was used to co-register the corresponding images across all three wavelengths.

The registered intensity image stacks (260, 280, and 300 nm wavelength images) for each FOV were used to obtain pseudo-RGB colorized images. To form the pseudo-colorized images, each color channel (i.e., Red (R), Green (G), and Blue (B) channels) was formed according to optimized weights (w) and gamma (γ) values by comparing the color representation of each blood cell to their stained counterparts based on the following equations:

$$R = w_R \times I_{260}^{\gamma R} \quad (1)$$

$$G = w_G \times I_{280}^{\gamma G} \quad (2)$$

$$B = w_B \times I_{300}^{\gamma B} \quad (3)$$

The colorized images were then transformed to the HSV color-space, a constant hue offset of +0.05 was applied, and converted back to RGB color-space. This pseudo-colorization scheme transforms the grayscale multi-spectral images (i.e., the RGB channel images) into a single pseudo-color image in which blood cells appear with colors that accurately mimic those in a conventional Giemsa stained image.

Stitching of pseudo-colorized images was performed using the Grid/Collection stitching plugin[35] of the Fiji[36] software that calculates the overlap between each tile and linearly blends them into a single wide-field image. The obtained wide-field pseudo-colorized images were then exported to the Zoomify format (Zoomify Inc., 2018) that enables viewing of large images using a standard web browser and uploaded to a custom-designed website for easy access and viewing by a clinical review panel.

Figure 2:
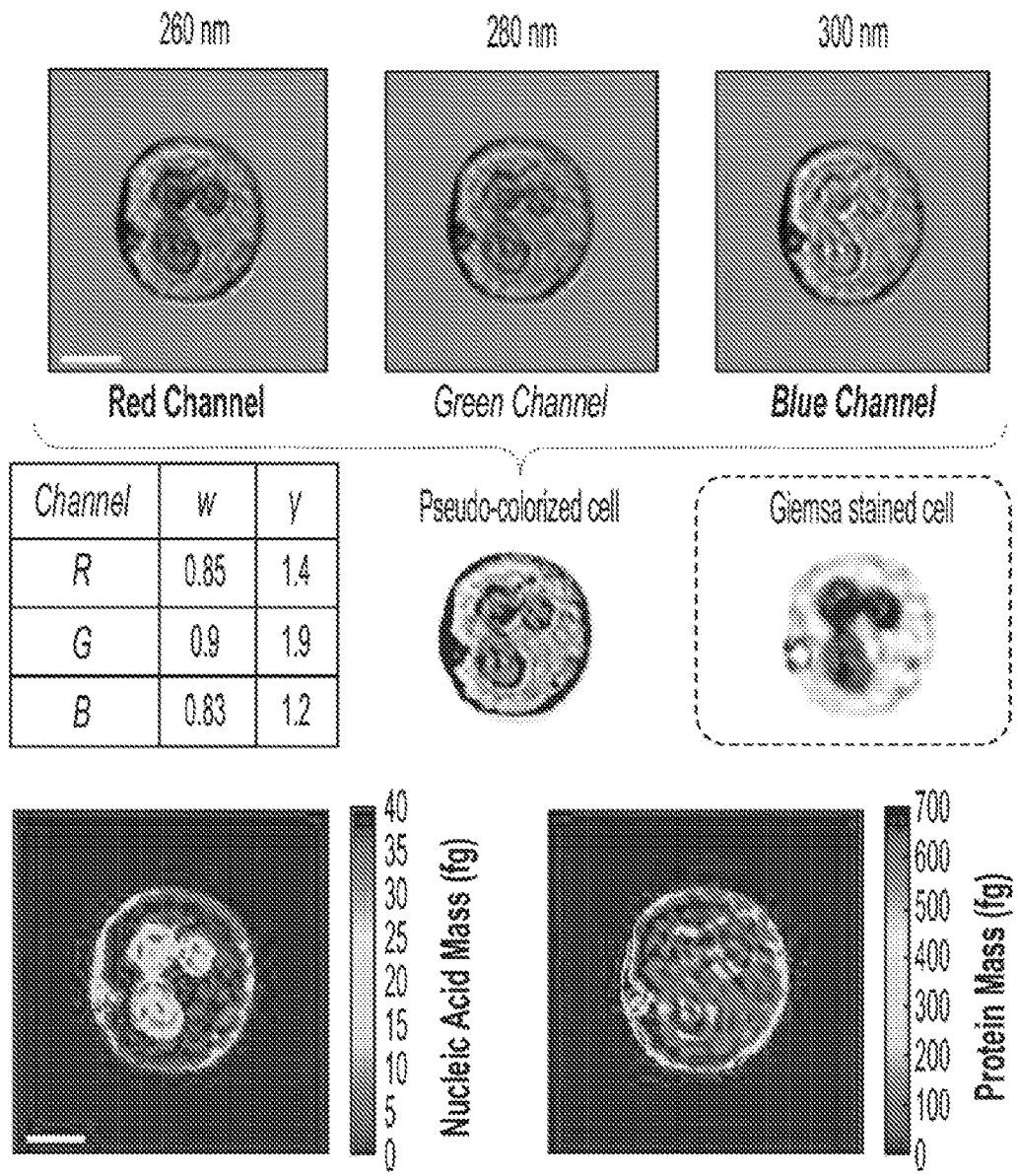
FIG. 2 shows multi-spectral images generated by the system in FIG. 1, and a colorized image based thereon in accord with a pseudo-colorization scheme; with a comparative Giemsa stained image of the same cell.

FIG. 2 shows examples of multi-spectral images that were generated from the live unlabeled blood cells with the system 100, along with a colorized UV image and a corresponding Giemsa stained bright-field image, each generated according to the foregoing setup. The scale bar in FIG. 2 is equal to 5 μm. In this example, the red channel images were generated with an optimized weight of 0.85 and gamma-value of 1.4; the green channel images were generated with an optimized weight of 0.90 and gamma-value of 1.9; and the blue channel images were generated with an optimized weight of 0.83 and gamma-value of 1.2. The red channel images at 260 nm reveal unique structural details from cell nuclei where densely packed nucleic acids are abundant[24,30], and the green channel images at 280 nm illustrate the distribution of proteins present in the cell nucleus periphery as well as the cytoplasm[30]. The blue channel images at 300 nm show a uniform low nuclear and cytoplasmic absorption, and were used as a counterstain in the pseudo-colorization scheme. The grayscale multi-spectral images (i.e., the RGB channel images) were then transformed into a single pseudo-color image with colors mimicking those in the comparative Giemsa stained image.

Figure 3:
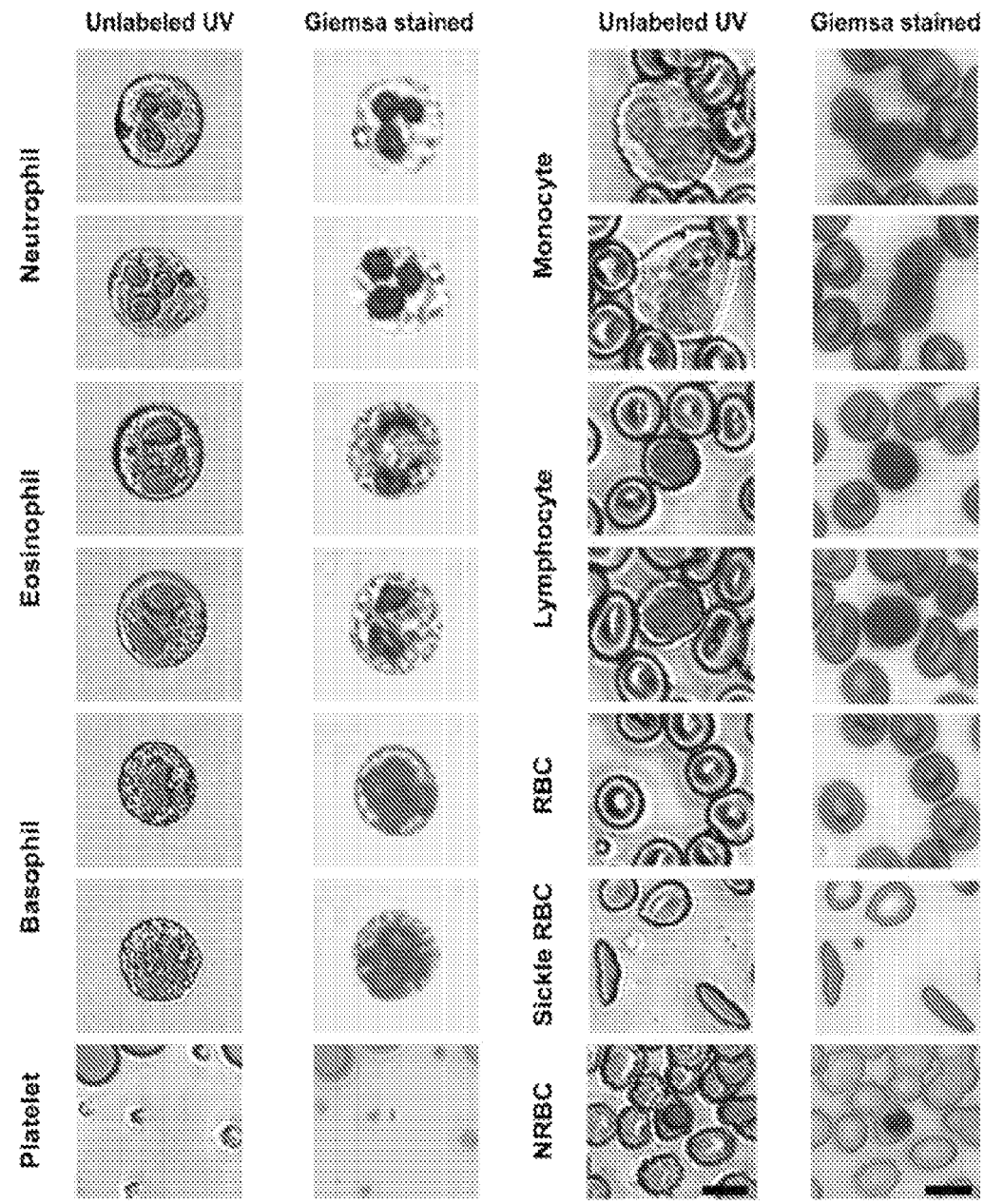
FIG. 3 shows a mosaic collection of different blood cell types imaged using the system in FIG. 1, and colorized based on the pseudo-colorization scheme; with comparative Giemsa stained images of the same cells.

FIG. 3 shows a mosaic collection of different blood cell types imaged using the system 100, with those images further colorized based on the pseudo-colorization scheme and presented side-by-side with comparative Giemsa stained images of the same cells. The scale bar in FIG. 3 is equal to 7 μm. As can be seen in the illustrated examples, the present invention enables the production of pseudo-colorized images that illustrate characteristic features of significant importance for blood cell phenotyping and differentiation, with the unique colors of each cell type originating from spectral absorption differences of various cellular biochemical components. For example, absorption of nucleic acids in leukocyte nuclei gives rise to the well-known distinctive violet color which can also be observed in their Giemsa stained images. In addition to nuclear contrast, unlabeled UV images according to the present invention highlight key cytoplasmic color differences which mainly stem from the different levels of protein absorption present in the nucleus periphery[30]. A noteworthy instance of such color contrast can be realized in eosinophils where protein absorption in the eosinophilic granules, abundant in the cytoplasm of these cells, results in a unique orange hue as illustrated in FIG. 3. Apart from color differences, pseudo-colorized UV microscopy images according to the present invention also reveal detailed cellular structures that are often critical for diagnosis and monitoring of blood diseases. Sickle cell anemia is a prominent example where deformed crescent-shaped RBCs become abundant in blood. Such deformation is clearly identifiable in the unlabeled UV images of sickled red cells in FIG. 3.

Thus, the pseudo-colorization scheme according to the present invention provides a simple and quick way of displaying the multi-spectral unlabeled UV images that is comparable to the conventional and widely-used bright-field microscopy images of Giemsa stained samples, though without requiring the complexities of standard fixing and staining protocols.

The present invention also provides for the calculation and quantification of RBC hemoglobin (Hb) in individual RBCs. Conventionally, quantification of RBC Hb mass is routinely performed in clinical hematology analysis by measuring the mean corpuscular hemoglobin (MCH) using hematology analyzers. MCH refers to the total Hb mass averaged over the total number of RBCs and is used for monitoring and diagnosis of many conditions such as anemias as well as thalassemia. Deviation of MCH values from a normal range (i.e., 29.5±2.5 pg)[1] is a marker that aids clinicians in diagnostic decision making process.

The present invention, with the unique capabilities of the deep-UV microscopy technique for quantitative analysis of cellular biochemical mass, enables the calculation of a total Hb mass as the dominant biochemical present (97% dry-mass fraction)[31] in individual RBCs in blood samples collected from healthy donors as well as sickle cell disease (SCD) patients. The MCH was obtained for 40 cells that were extracted from samples of healthy donors and SCD patients (two patients sample in each group, n=20) and used the 300 nm wavelength images for mass quantification.

The nucleic acid and protein mass were quantified based on the calculation of optical density (OD=$-\ln(\tilde{I}/\tilde{I}_0)$), which is obtained by normalizing each UV image ($\tilde{I}$) by a reference background image taken from an empty area on the sample at each wavelength. The OD maps obtained at 260 nm and 280 nm wavelengths are then used to calculate the mass maps assuming a linear contribution of species at each wavelength according to the following equation:

$$OD^{wavelength\ n} = (\varepsilon_{nuc.\ acid}^{wavelength\ n})lc_{nucleic\ acid} + (\varepsilon_{protein}^{wavelength\ n})lc_{protein} \quad (4)$$

where $\varepsilon$ is the extinction coefficient, l is the optical path length, and c is the species concentration[6]. Based on OD values for the two wavelengths, a set of equations are generated and solved for the concentration-pathlength products (lc terms) at each pixel. In these calculations, average extinction coefficients at 260 nm and 280 nm for nucleic acid were ($\varepsilon_{260}$=7,000 M$^{-1}$ cm$^{-1}$, $\varepsilon_{280}$=3,500 M$^{-1}$ cm$^{-1}$) and for protein were ($\varepsilon_{260}$=36,057 M$^{-1}$ cm$^{-1}$, $\varepsilon_{280}$=54,129 M$^{-1}$ cm$^{-1}$)[37] and average OD values over the bandwidth of the UV filters. There was assumed average molar masses of 52,728 Da for protein and 330 Da for nucleic acids to obtain mass values at each pixel.

When calculating the Hb mass in RBCs, the OD at 300 nm wavelength and the molar extinction coefficient of oxygenated Hb ($\varepsilon_{300}$=65,972M$^{-1}$ cm$^{-1}$)[26,38] were used to calculate the concentration-pathlength products (lc terms) at each pixel; and these values were then integrated over the entire cell area to obtain the total mass for each cell. Student's t-test was used for comparison of populations in the quantitative analysis of Hb mass in RBCs. JMP Pro software (version 14.0; SAS Institute Inc., Cary, NC) and MATLAB (MathWorks) was used for all statistical analyses.

Figure 4:
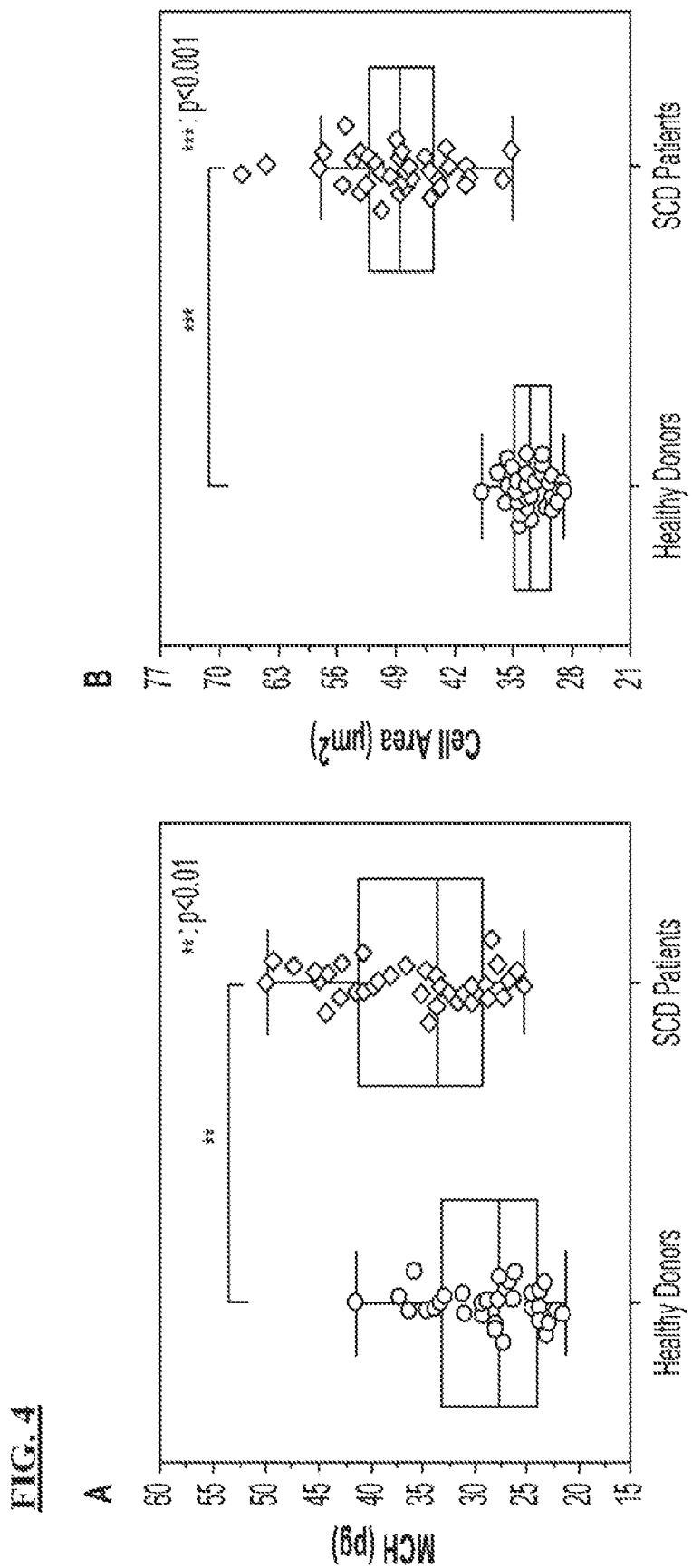
FIGS. 4a-4d shows hemoglobin quantification in healthy and sickled RBCs, including: (a) MCH values obtained from two healthy patients (n=40) and two SCD patients (n=40) samples; (b) cell area values from the healthy and SCD donors; (c) average Hb mass per square area for healthy and SCD RBCs; and (d) a scatter plot of MCH versus cell area for the healthy and SCD samples, with insets showing examples of RBC Hb mass maps.
Figure 4:
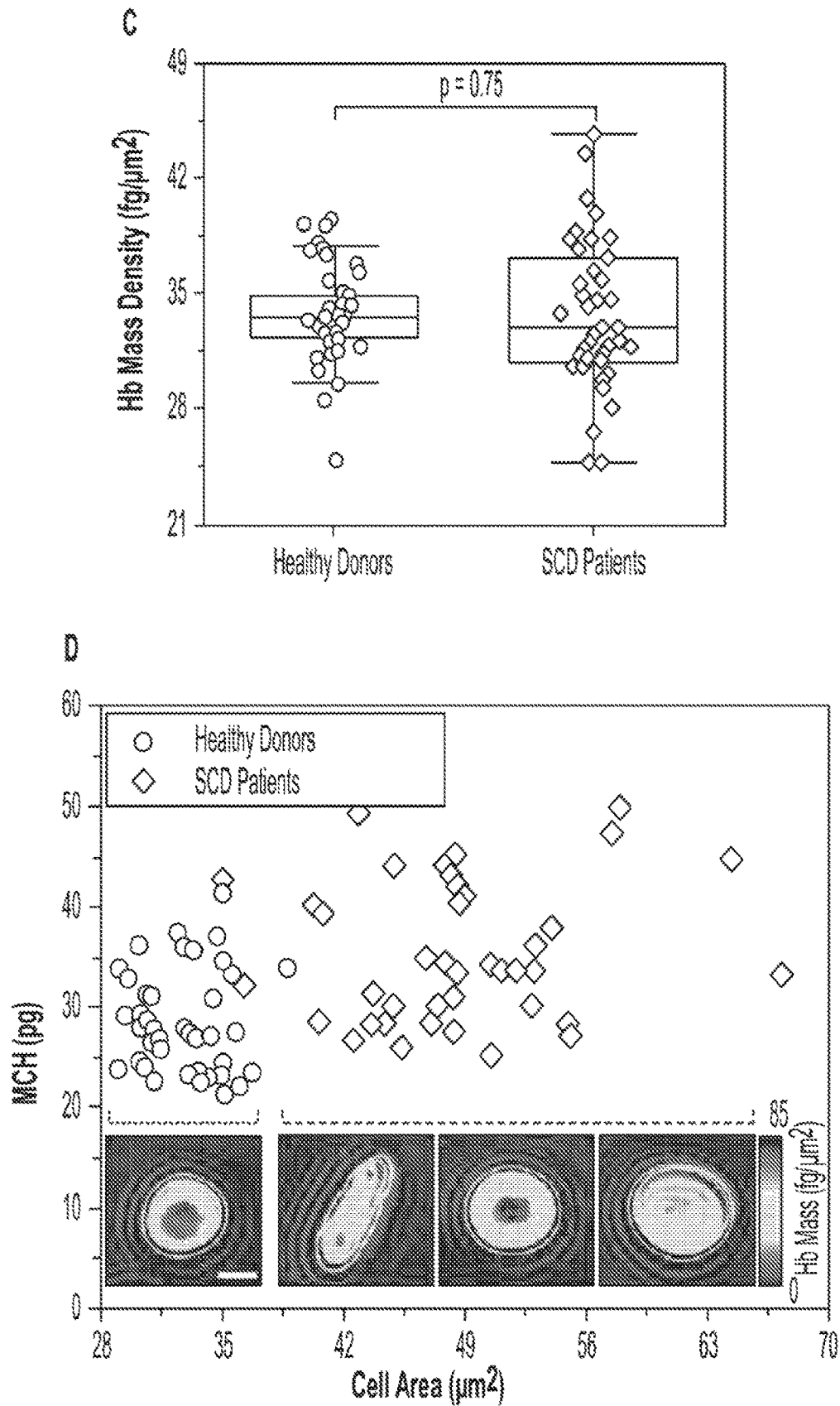

FIG. 4a shows the retrieved MCH values for the working example. In this instance, the MCH for healthy donor RBCs were found to have a mean of 28.6±5.1 pg, and MCH values for SCD donor RBCs were found to have a mean of 35.4±6.9 pg. These values suggest a slightly higher mass values for the sickle RBCs, showing a statistically significant difference when compared to the healthy RBCs (p<0.01). This slight increase in the average MCH in SCD patients is consistent with prior studies reporting on the production of larger RBCs, based on cell area values from healthy and SCD donors, as shown in FIG. 4b, with the same Hb concentration in patients under treatment with hydroxyurea[31,32]. FIG. 4c shows average Hb mass per square area for the healthy and SCD RBCs. The presence of larger RBCs in SCD samples is evident in FIG. 4d, which shows a scatter plot of MCH versus cell area for healthy and SCD samples, with insets showing examples of RBC Hb mass (in femtograms) maps. The scale bar in the inset is 5 As can be seen from the data in the scatter plot, sickle RBCs deviate towards larger cell areas, with a larger diameter, for all the different morphologies of SCD RBCs.

Differential cell counting is a useful part of laboratory hematological analysis for monitoring and diagnosis of blood diseases. Disease-induced alterations in population of blood cells are often investigated using automated cell counting devices (e.g., flow cytometers) which are able to classify cells based on their morphological properties such as size and granularity or fluorescence intensity of cell-specific dyes. Flow cytometers measure the forward and side scattering of a laser source as it interacts with cells, the former determines cellular size while the latter gives a measure of granularity[33]. Although automated hematology analyzers are able to rapidly analyze several samples, they are labor-intensive, costly, and require many reagents.

Systems 100 according to the present invention may be further configured for delivering label-free, accurate, and consistent blood cell differential counting that would circumvent the limitations of conventional systems in clinical settings as well as point-of-care applications. This may be achieved by providing an unsupervised cell classifier for differential cell counting, with the cell classifier being developed through machine learning for perform a five-part WBC differential.

In one non-limiting working example, an unsupervised cell classifier was trained by extracting 58 different features from UV multi-spectral images (i.e., 260, 280, and 300 nm) obtained from 100 WBCs (20 lymphocytes, 20 monocytes, and 20 of each PMNL subtype), as well as biochemical masses from whole cell, cell nucleus, and cytoplasm. The extracted features include those presented in the following table:

| Feature | Description |
| --- | --- |
| | Morphological |
| Area | Area contained by cell contour |
| Perimeter | Cell contour perimeter |
| Eccentricity | The ratio of the distance between the foci of the ellipse and its major axis length. An ellipse whose eccentricity is 0 is a circle, while an ellipse whose eccentricity is 1 is a line segment. |
| Circularity | Calculated by $4\pi \times$ (cell Area)/perimeter2. Circularity of a circle is 1. |
| Major/Minor Axis Length | Length of the major/minor axis of the ellipse that has the same normalized second central moments as the cell contour |
| Extent | Ratio of pixels in the cell contour to pixels in the total bounding box. |
| Solidity | Ratio of contour area to its convex hull area |
| Second Momentum | Euclidian distance between geometric centroid and each pixel averaged over the whole region. |
| | Statistical |
| Mean | Sum of pixel values over the total number of pixels in the region. |
| Skewness | Skewness is a measure of the asymmetry of the data around the sample mean. If skewness is negative, the data spreads out more to the left of the mean than to the right. If skewness is positive, the data spreads out more to the right. The skewness of the normal distribution (or any perfectly symmetric distribution) is zero. |
| Kurtosis | Kurtosis is a measure of how outlier-prone a distribution is. The kurtosis of the normal distribution is 3. Distributions that are more outlier-prone than the normal distribution have kurtosis greater than 3; distributions that are less outlier-prone have kurtosis less than 3. |
| Entropy | Entropy is a statistical measure of randomness that can be used to characterize the texture of the input image. Defined as sum of the normalized histogram counts times their log. |
| Standard Deviation | Square root of the difference between each pixel value and average pixel values squared over the number of pixels minus one |
| | GLCM |
| Contrast | Intensity contrast between a pixel and its neighbor based on GLCM of the image. |
| Correlation | Measure of how correlated a pixel is to its neighbor over the whole image. Correlation is 1 or −1 for a perfectly positively or negatively correlated image. |
| Energy | The sum of squared elements in the GLCM of the image. Energy is 1 for a constant image. |
| Homogeneity | Measures the closeness of the distribution of elements in the GLCM to the GLCM diagonal. Homogeneity is 1 for an image with diagonal GLCM. |
| | Mass |
| Protein | Average protein mass (in fg) calculated based on the description in Methods section. |
| Nucleic acid | Average nucleic acid mass (in fg) calculated based on the description in Methods section. |

These foregoing features were reviewed and classified by a board-certified hematologist. Morphological, statistical, and textural features were extracted based on a gray-level co-occurrence matrix (GLCM), from processing of intensity images obtained at 260 nm wavelength. Average biochemical masses from cells were also obtained using the 260 nm and 280 nm images according to the described method for quantification of biochemical masses.

Figure 5:
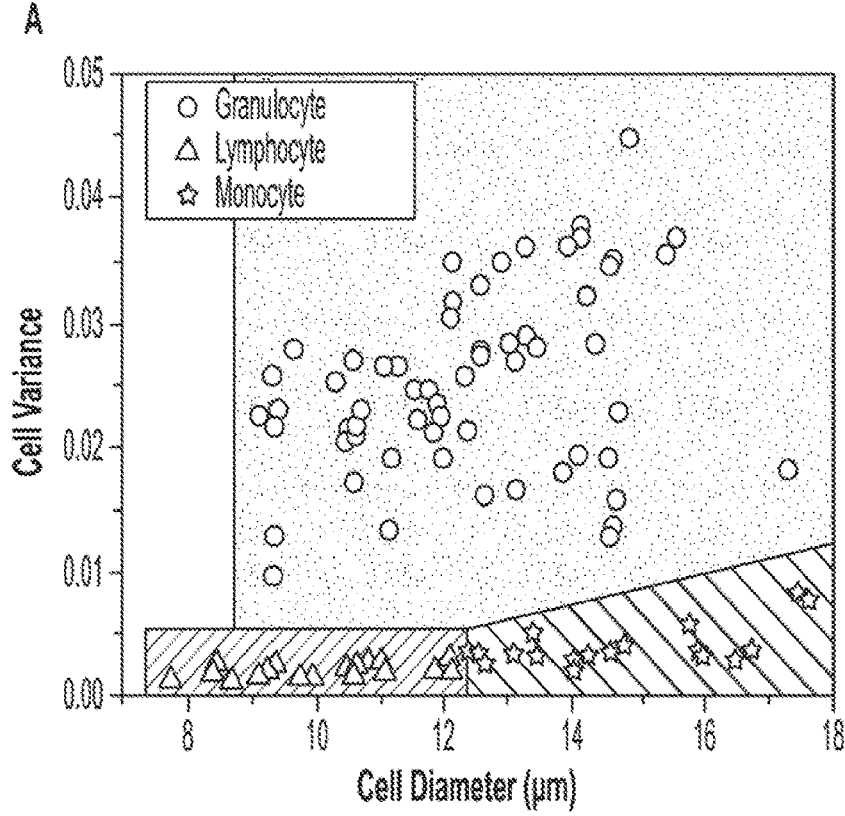
FIG. 5a-5c show a machine learning-based five-part WBC differential, including: (a) cellular intensity variance plotted against cell diameter to perform a three-part WBC differential among PMNLs, Lymphocytes, and Monocytes; (b) receiver operating characteristic (ROC) curves associated with a machine learning-based PMNL classification; and (c) a scatter plot of the PMNL subtypes based on the three top-ranked features.
Figure 5:
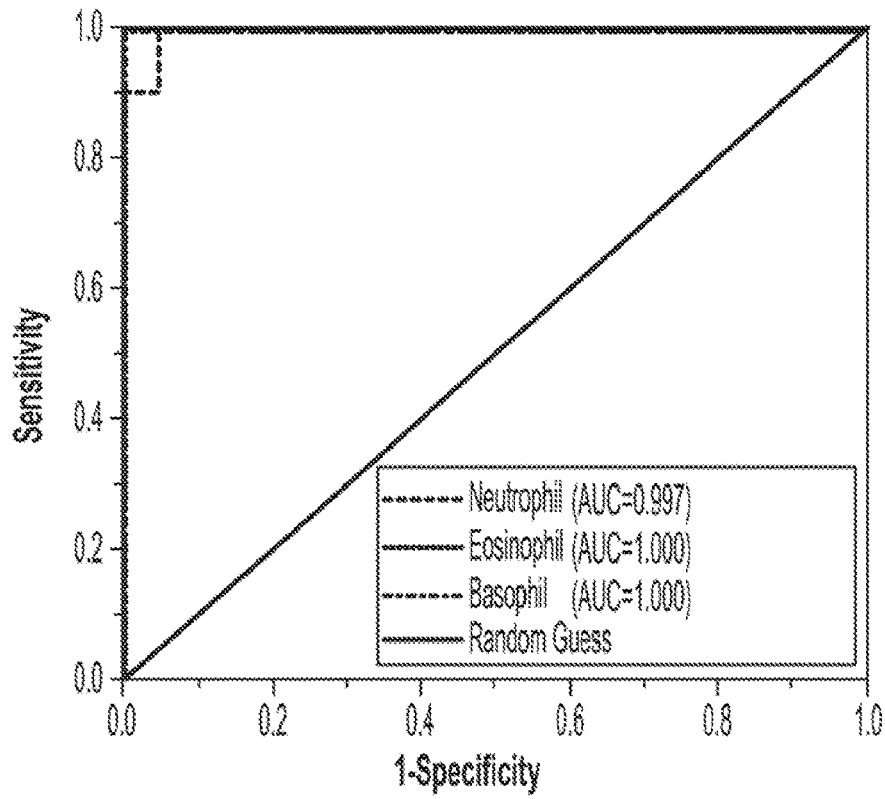
Figure 5:
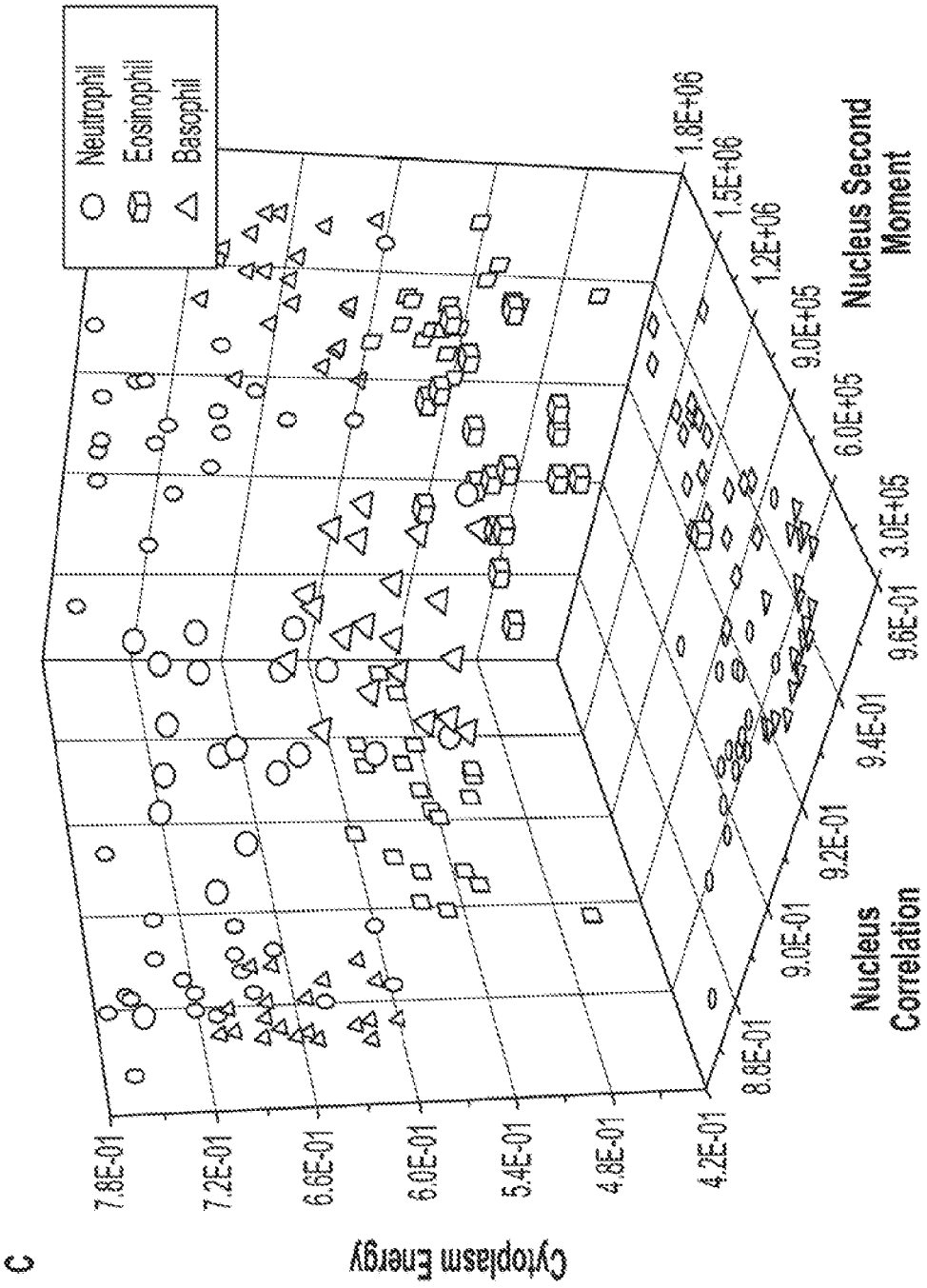

Initially, a three-part differential was applied to classify lymphocytes, monocytes, and PMNLs based only on size and granularity. As depicted in FIG. 5a, a clear class separation can be observed between these three cell types as a plot of the cell diameter against the variance of the intensity values throughout the cell. As can be seen, PMNLs with a higher granularity produce larger variations in intensity which leads to a higher pixel value variance compared to lymphocytes and monocytes. In addition, the larger monocytes populate within an area that corresponds to diameters larger than lymphocytes which is used for their separation. This simple analysis resembles the forward versus side scattering plots of WBCs obtained via flow cytometry and is in agreement with the well-known morphological and textural properties of these cell types[33].

To complete the five-part differential, a machine learning algorithm was constructed based on a Gaussian support-vector machine (SVM) trained using the extracted features from PMNLs. The trained SVM model was evaluated according to a five-fold cross-validation scheme that randomly partitions the dataset into five equal-sized subsamples. A subsample was utilized for validation and testing the model while the remaining subsamples were used as training data. This process was repeated five times, with each of the five partitions used only once as the validation data. By doing this, we ensured that the whole dataset was used for both training and validation.

Figure 6:
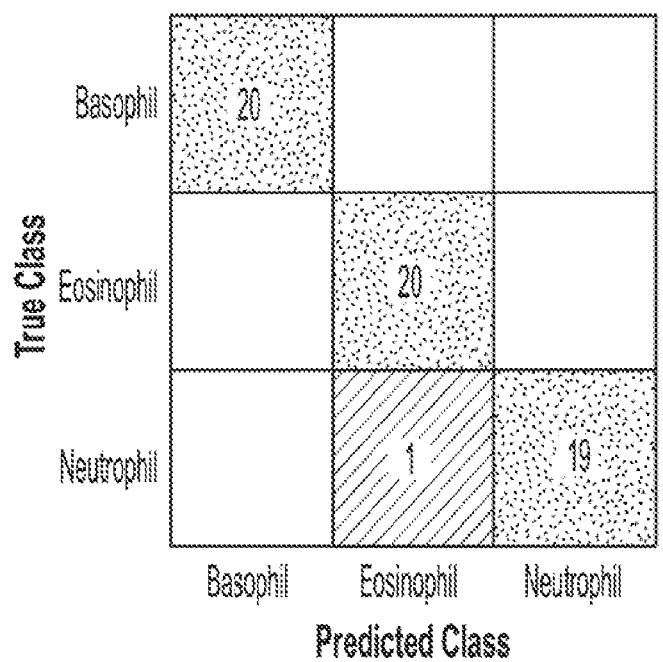
FIG. 6 shows a confusion matrix for a multi-wavelength support-vector machine (SVM) model displaying classification results from the system in FIG. 1.

A number of performance metrics were obtained to assess the performance of the cell classification model, including: accuracy which is the ratio of number of correct predictions to the total number of input dataset; sensitivity which determines the percentage of true positive classification events; and specificity that measures the percentage of true negatives determined by the model. The receiver operating characteristic (ROC) curves were also used for graphical illustration of model performance. With these metrics, the validation scheme was found to yield an accuracy of 98.3%, a sensitivity of 95%, and a specificity of 100% for classification of PMNL subtypes (i.e., neutrophils, eosinophils, and basophils). The ROC curves and confusion matrix associated with the machine learning-based PMNL the classification, depicted in FIGS. 5b and 6, further illustrate the model's accuracy in identify PMNLs, having misclassified only one cell.

A feature ranking algorithm was then applied based on the area of ROC curves to the feature set and machine training was performed based on the three top-ranked features. The extracted features were ranked using a ranking algorithm (rankfeatures function, MATLAB) that calculates the area between the ROC curve and the random classifier slope, and three features that yielded the highest ROC areas were picked for training of the single-wavelength classifier.

Figure 7:
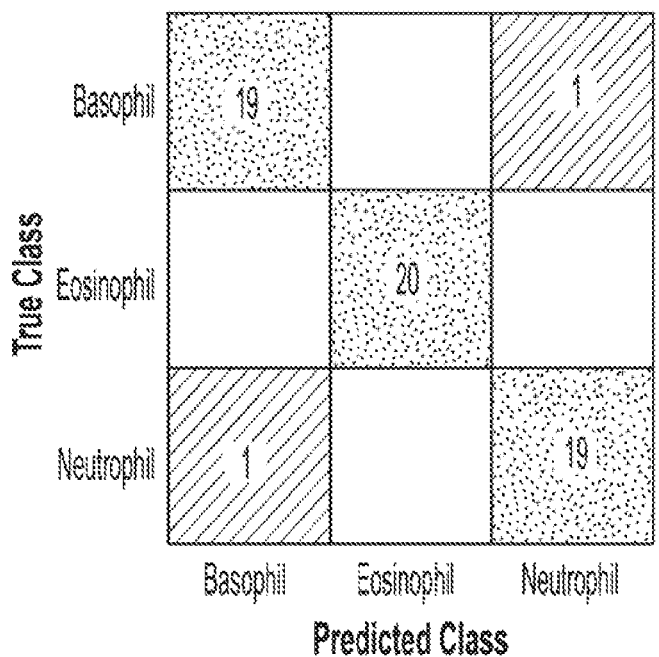
FIGS. 7a-7b show cell classifying results for a single-wavelength SVM model, including: (a) a confusion matrix; and (b) ROC curves.
Figure 7:
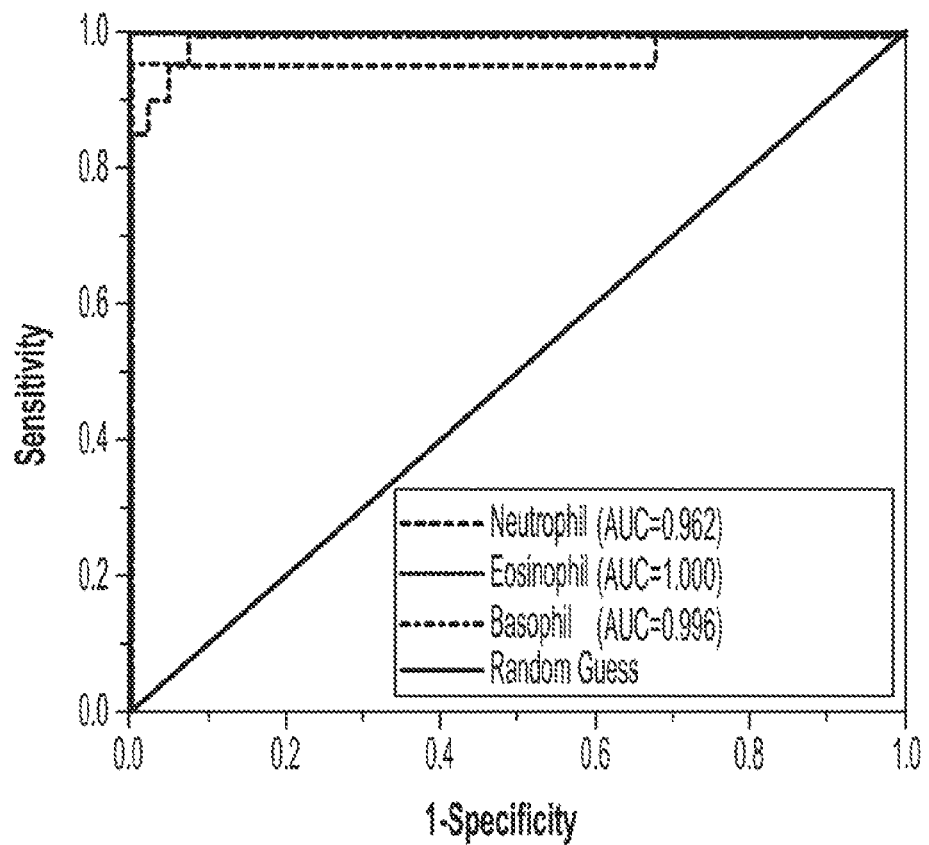

In the working example, the algorithm selected the cytoplasm energy, nucleus correlation, and nucleus second momentum as the feature set resulting in the highest class separation between the three cell types. FIG. 5c shows a scatter plot of the PMNL subtypes based on these three top-ranked features. Remarkably, it was found that all of the top-ranked features required to train the model can be extracted from only a single wavelength (i.e., 260 nm images). Thus, a compact hematology analysis device may be enabled for a five-part differential with high accuracy using only images acquired at a single wavelength. Performance of the trained classifier was slightly lower than the full model with an accuracy of 96.7%, a sensitivity of 95%, and a specificity of 97.5%. The confusion matrix and ROC curves for this single-wavelength SVM model are shown in FIGS. 7a-7b, respectively.

The pseudo-colorized UV images reveal unique morphological and color features for each blood cell type, making them suitable for use as an alternative disease diagnostic tool in place of existing visual inspection methods based on Giemsa stained smears. This was established by comparative image testing of blood smears prepared from healthy donor samples (4 samples) relative to blood smears prepared from samples collected from patients diagnosed with different levels of thrombocytopenia (5 samples) and sickle cell anemia (4 samples). Advance identification of the blood disorders were made based on CBC results carried out at the collection site.

Figure 8:
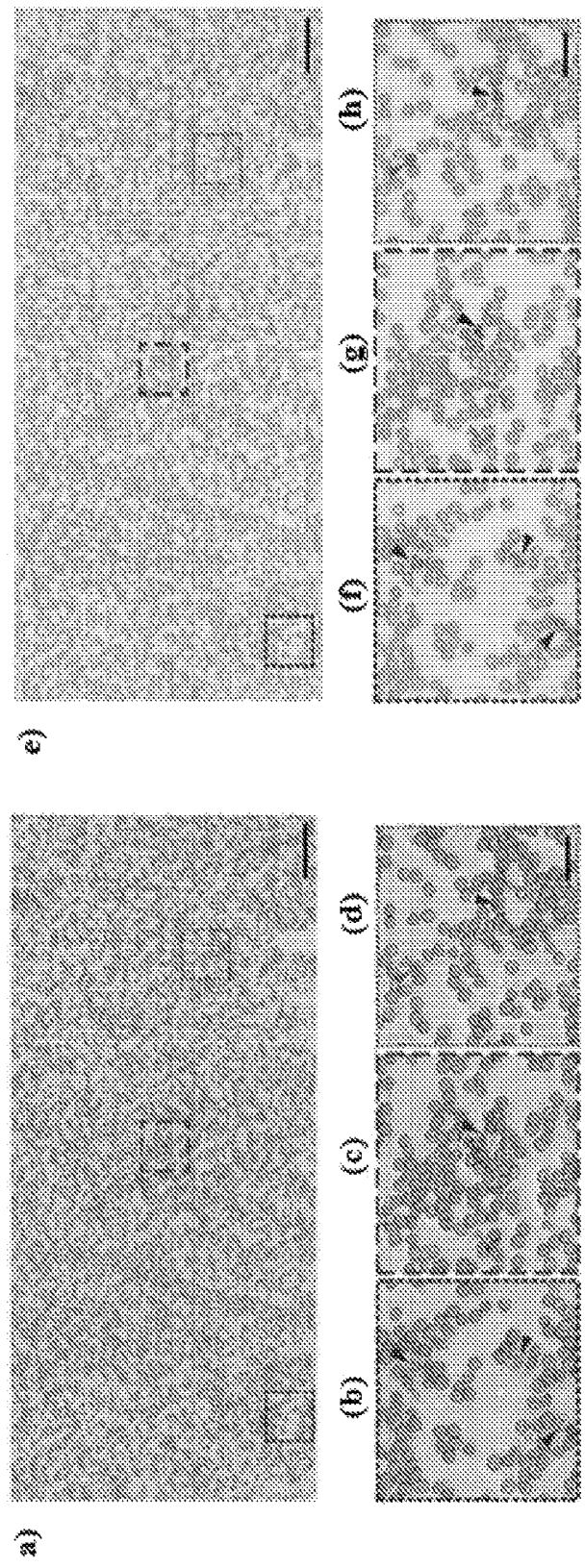
FIGS. 8a-8h show comparative microcopy images of blood smear samples, including: (a) a wide-field pseudo-colorized UV image of a sample collected from a sickle cell anemia patient; (b) a first magnified inset from the wide-field pseudo-colorized UV image; (c) a second magnified inset from the wide-field pseudo-colorized UV image; (d) a third magnified inset from the wide-field pseudo-colorized UV image; (e) a wide-field bright-field microscopy image of the same sample pictured in the wide-field pseudo-colorized UV image, though after fixing and staining with Giemsa stain; (f) a first magnified inset from the wide-field bright-field microscopy image, corresponding to the first magnified inset from the wide-field pseudo-colorized UV image; (g) a second magnified inset from the wide-field bright-field microscopy image, corresponding to the second magnified inset from the wide-field pseudo-colorized UV image; and (h) a third magnified inset from the wide-field bright-field microscopy image, corresponding to the third magnified inset from the wide-field pseudo-colorized UV image.

In this testing, wide-field colorized UV images were constructed from a 1×2 mm area on the blood smear samples to ensure that enough cells were included for a reliable diagnosis; and bright-field microscopy images were also acquired from the same areas after fixing and staining. This was done in accord with the methods discussed earlier. The wide-field pseudo-colorized UV image and the corresponding Giemsa stained wide-field bright-field microscopy image are shown in FIGS. 8a and 8e. The scale bars in these images are equal to 100 μm. First, second and third select magnified sections of the wide-field pseudo-colorized UV image are shown in FIGS. 8b-8d. FIG. 8b identifies instances of neutrophils; FIG. 8c identifies instances of neutrophils and sickled RBCs; and FIG. 8d identifies instances of neutrophils and lymphocytes. FIGS. 8f-8h show magnified sections of the Giemsa stained wide-field bright-field microscopy image, corresponding with the first, second and third selected magnified section in FIGS. 8b-8d, respectively, and identifying common cellular features. The scale bar for the images in FIGS. 8b-8d and 8f-8h is equal to 30 μm.

Careful inspection of the magnified images reveals that the UV pseudo-colorized images in FIGS. 8a-8d highlight key cellular features with outstanding clarity and contrast compared to conventional stained images in FIGS. 8e-8h, proving the potential for use of UV pseudo-colorized images in clinical diagnosis based on examination of blood smears.

Sufficiency of the pseudo-colorized UV images for use as a diagnostic tool was tested through a web-based survey in which a panel of fourteen board-certified hematologists, blinded to the patients' conditions and clinical histories, were presented with a randomly distributed and de-identified set of 26 wide-field images (13 UV and 13 bright-field images) From healthy, thrombocytopenia, and sickle cell anemia samples, with each image being accompanied by an online questionnaire in which the hematologists provide assessment of the population and morphology of each blood cell type and respond to questions pertaining to their overall diagnosis, diagnostic confidence, and diagnostic quality of the images. Diagnostic quality was defined as whether the hematologists felt that the image quality enabled them to make a proper diagnosis. Diagnostic confidence was defined as how certain the reviewers felt about their assessment. Questionnaire responses were then recorded automatically and used for statistical analysis. The clinical panel review protocol was approved by the Institutional Review Board of Georgia Institute of Technology (protocol no. H19389).

The hematologist panel's diagnostic performance was assessed by calculating the concordance between their diagnosis (healthy vs thrombocytopenia vs sickle cell anemia) based on UV and bright-field images using Cohen's kappa[39], assuming that the data are categorical and based on the fact that the UV and bright-field images were taken on the same data. Cohen's kappa values were also calculated for the diagnosis from UV and bright-field versus ground truth (based on CBC performed at the collection site, Emory Hospital) to assess how well each panel member's diagnosis correlates with CBC. Concordance was also calculated between every two hematologists to determine the reliability of their assessment. The results of the panel review with Cohen's kappa values and accuracy are shown in the following table:

| Patient blood sample type | Imaging modality | No. of wide-field images | Accuracy % | Concordance (Cohen's kappa, κ) |
|---|---|---|---|---|
| Healthy | UV | 4 | 85.0 | 0.84 |
|  | BF | 4 | 85.0 |  |
| Thrombocytopenia | UV | 5 | 76.2 | 0.75 |
|  | BF | 5 | 68.2 |  |
| SCD | UV | 4 | 80.0 | 0.90 |
|  | BF | 4 | 75.2 |  |
| Combined | UV | 13 | 80.4 | 0.83 |
|  | BF | 13 | 76.5 |  |

BF, bright-field.

As can be seen, there was near-perfect concordance between the two inspection methods for determining the patient's condition; and that the hematologists were able to perform diagnosis with reasonable accuracy based on UV and bright-field images, respectively.

The near-perfect concordance between diagnoses made based on the two modalities suggest that the hematologist panel was able to derive diagnoses from the wide-field pseudo-colorized UV images with reasonable accuracy which are highly concordant with those made based on standard visual inspection methods. This is indicative that the pseudo-colorized UV images are highly suitable for use as an alternative to the conventional bright-field microscopy in clinical diagnostics and screening.

Figure 9:
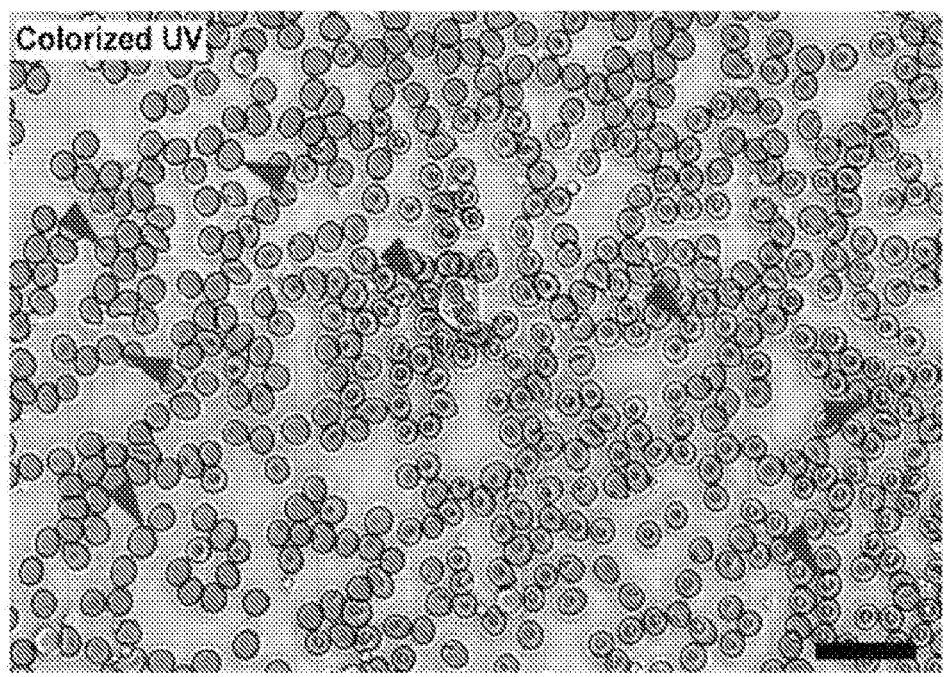
FIGS. 9a-9b showing a transition region with RBCs that have a biconcave shape (gray arrowheads) and RBCs that do not have the biconcave shape (blue arrowheads), including: (a) a UV colorized image; and (b) a bright-field image.
Figure 9:
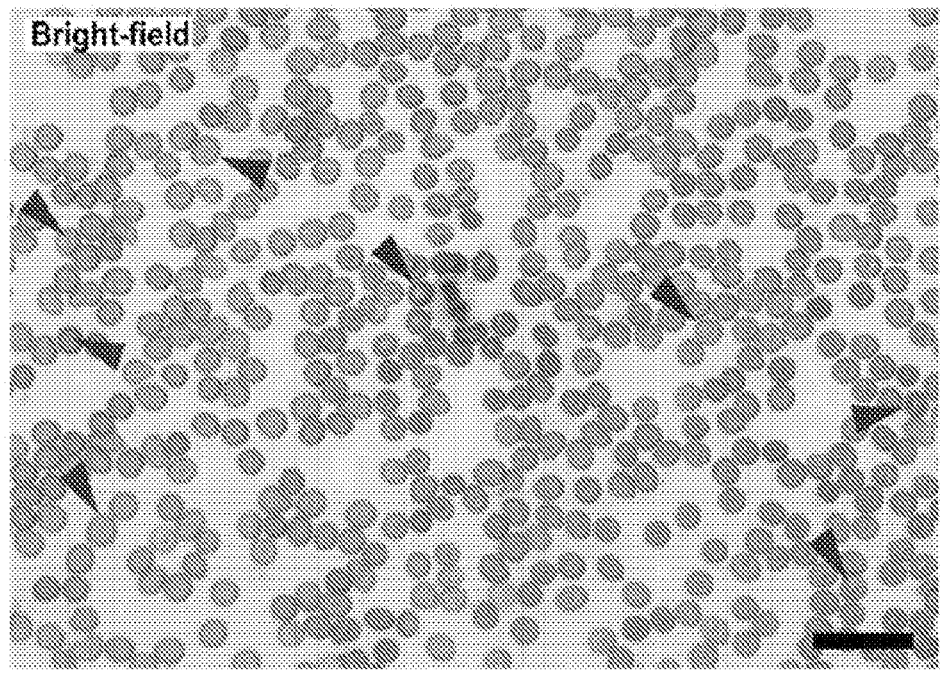

While both the pseudo-colorized UV images and the bright-field images enabled highly accurate diagnosis, some discrepancies occurred in determination of patient condition. Such discrepancies generally arise from differences in the appearance of RBCs that might lose their typical biconcave shape towards the end region of the monolayer area of the smear. An example of this is shown in FIGS. 9a-9b, in which UV colorized and bright-field images of the transition region show RBCs with the biconcave shape (gray arrowheads) and without the biconcave shape (blue arrowheads). The scale bars in these figures are 30 µm. This is a common issue with blood smears, even when stained samples are inspected via bright-field microscopes, which results in a misdiagnosis and confusion with another condition known as spherocytosis—a condition where RBCs lose their biconcavity and turn into spherically shaped cells. This issue can be mitigated by ensuring that imaging is performed within a central region of the monolayer area where RBCs maintain their natural shape.

Figure 10:
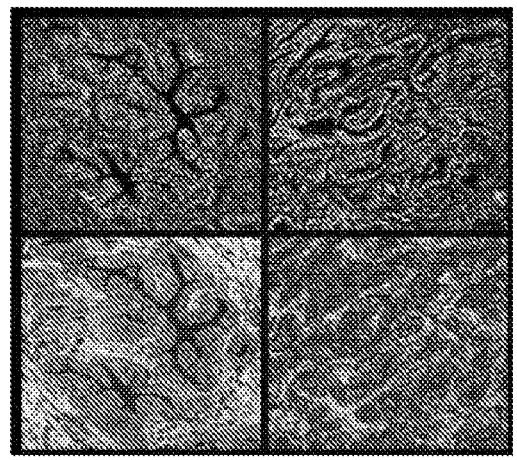
FIG. 10 shows two different colorization schemes based on the UV images of tissues, each highlighting different structures in the imaged tissues.

FIG. 10 demonstrates the use of UV microscopy in histopathology and tissue phenotyping. As shown in FIG. 10, the UV images acquired at 220 nm, 255 nm, 280 nm and 300 nm were synthesized using principle component analysis to produce two different types of color images based on their biochemical composition, each highlighting different structures. In this figure, the images on the top left and bottom left are of the same structure, though with different color code—likewise, the top right and bottom right are of the same structure, though with different colorization mode. In this example, the top images use green highlights to identify cell nuclei; the bottom images use yellow highlights identify stroma, and red highlights to identify glandular tissue. The differences in red hue indicate phenotypical differences in glands.

The present invention thus provides systems and methods for performing quantitative and qualitative assessment of blood cells using multi-spectral deep-UV microscopy images without the need for standard fixing and staining methods. Furthermore, with a pseudo-colorization technique according to the present invention, there can be produced color-accurate images that mimic those observed in conventional Giemsa staining, enabling simple, fast, and reliable visual inspection that is suitable for use in clinical and point-of-care settings. In addition, through use of a supervised machine learning algorithm according to the present invention, there can be performed a quantitative analysis and a five-part differential of WBCs which is commonly done using expensive and laborious methods such as flow cytometry. Accurate classification of WBCs subtypes can be achieved by training a classification algorithm based on a combination of features that represent the morphological and biochemical properties of cells extracted from information-rich multi-spectral UV images. The present invention also simplifies the classification scheme by training the model based on a limited number (e.g., three) of top ranked features which can be extracted from a single wavelength image (e.g., 260 nm). As a result, systems and methods according to the present invention can be implemented for clinical or point-of-care hematology analysis, able to provide differential blood cell counts in a simple, low-cost, and prompt manner.

While the single-wavelength-based classifier may have a slightly lower accuracy compared to a full model, it nonetheless permits the elimination of any need for multispectral image stacks that would require a more complex and expensive system consisting of an accurately calibrated Z-axis stage and a UV filter wheel to tune the imaging wavelength. As a result, systems according to the present invention may be made with deep-UV light emitting diodes (LEDs) and UV-sensitive sensors, thereby enabling a low-cost and compact hematological analysis device that is suitable for both clinical and point-of-care applications.

Systems and methods according to the present invention are also well-suited for integration into existing laboratory hematological analysis workflows, and may be used in conjunction with telemedicine technologies, providing clinicians with enough information to aid them in clinical decision-making processes. Moreover, systems and method according to the present invention may be combined with automated cell segmentation and classification techniques to enable implementation in a portable and easy-to-use in-home device, with significant potential to improve quality of life for patients with blood diseases, allowing reliable and accurate point-of-care monitoring and diagnosis.

Figure 11:
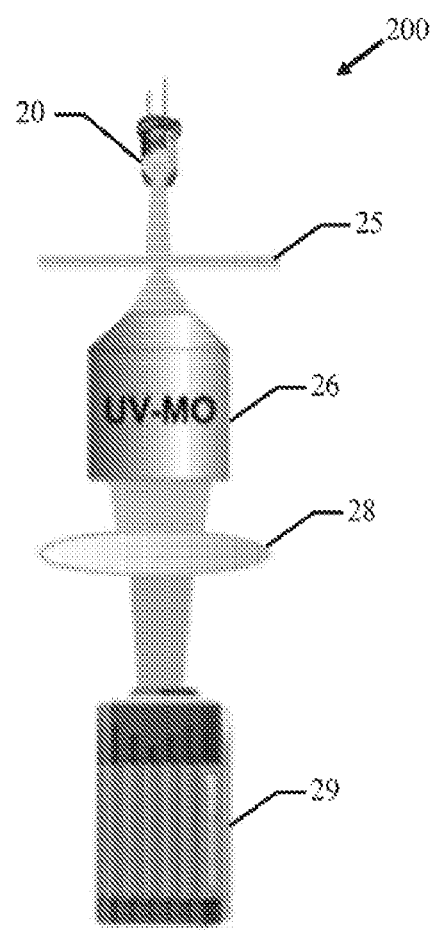
FIG. 11 shows another example of a system according to the present invention, with a simplified geometry that employs an LED in place of a broadband light source and filters.

FIG. 11 shows another example of a system 200 according to the present invention. In this example, the system is provided with a simplified geometry in which an LED 20 is used instead of a broadband light source and filters. In this example, output light from the LED 210 is directed to the sample 24. A UV microscope objective 23 is used for imaging, and the light is passed through a tube lens 21 before being captured by a UV-sensitive camera 29. In other examples, multiple LEDs at different spectral regions can also be implemented.

Although the present invention is described with reference to particular embodiments, it will be understood to those skilled in the art that the foregoing disclosure addresses exemplary embodiments only; that the scope of the invention is not limited to the disclosed embodiments; and that the scope of the invention may encompass additional embodiments embracing various changes and modifications relative to the examples disclosed herein without departing from the scope of the invention as defined in the appended claims and equivalents thereto.

To the extent necessary to understand or complete the disclosure of the present invention, all publications, patents, and patent applications mentioned herein are expressly incorporated by reference herein to the same extent as though each were individually so incorporated.

The present invention is not limited to the exemplary embodiments illustrated herein, but is instead characterized by the appended claims, which in no way limit the scope of the disclosure.

REFERENCES

1. Dacie, J. *Dacie and Lewis practical haematology.* (2006).
2. Winkelman, J. W., Tanasijevic, M. J. & Zahniser, D. J. A novel automated slide-based technology for visualization, counting, and characterization of the formed elements of blood a proof of concept study. *Arch. Pathol. Lab. Med.* 141, 1107-1112 (2017).
3. Larsson, A., Greig-Pylypczuk, R. & Huisman, A. Upsala *Journal of Medical Sciences* The state of point-of-care testing: a european perspective. The state of point-of-care testing: a European perspective. *Ups. J. Med. Sci.* 120, 1-10 (2015).
4. Majors, C. E., Pawlowski, M. E., Tkaczyk, T. & Richards-Kortum, R. R. Low-cost disposable cartridge for performing a white blood cell count and partial differential at the point-of-care. in 2014 *IEEE Healthcare Innovation Conference, HIC* 2014 10-13 (Institute of Electrical and Electronics Engineers Inc., 2014). doi:10.1109/HIC.2014.7038862
5. ZHENG, S., LIN, J., KASDAN, H. & TAI, Y. Fluorescent labeling, sensing, and differentiation of leukocytes from undiluted whole blood samples. *Sensors Actuators B Chem.* 132, 558-567 (2008).
6. van de Geijn, G. J. et al. Leukoflow: Multiparameter extended white blood cell differentiation for routine analysis by flow cytometry. *Cytom. Part A* 79 A, 694-706 (2011).

7. Chan, L. L., Wilkinson, A. R., Paradis, B. D. & Lai, N. Rapid Image-based Cytometry for Comparison of Fluorescent Viability Staining Methods. doi:10.1007/s10895-012-1072-y
8. Golan, L., Yeheskely-Hayon, D., Minai, L., Dann, E. J. & Yelin, D. Noninvasive imaging of flowing blood cells using label-free spectrally encoded flow cytometry. *Biomed. Opt. Express* 3, 1455 (2012).
9. Yoon, J. et al. Label-free characterization of white blood cells by measuring 3D refractive index maps. *Biomed. Opt. Express* 6, 3865 (2015).
10. Gonzalez, S., Sackstein, R., Anderson, R. R. & Rajadhyaksha, M. Real-time evidence of in vivo leukocyte trafficking in human skin by reflectance confocal microscopy. *J. Invest. Dermatol.* 117, 384-6 (2001).
11. Lange-Asschenfeldt, S. et al. Applicability of confocal laser scanning microscopy for evaluation and monitoring of cutaneous wound healing. *J. Biomed. Opt.* 17, 0760161 (2012).
12. Winer, M. M. et al. In vivo noninvasive microscopy of human leucocytes. *Sci. Rep.* 7, (2017).
13. Zharov, V. P., Galanzha, E. I. & Tuchin, V. V. In vivo photothermal flow cytometry: Imaging and detection of individual cells in blood and lymph flow. *J. Cell. Biochem.* 97, 916-932 (2006).
14. Ramoji, A. et al. Toward a spectroscopic hemogram: Raman spectroscopic differentiation of the two most abundant leukocytes from peripheral blood. *Anal. Chem.* 84, 5335-5342 (2012).
15. Verebes, G. S. et al. Hyperspectral enhanced dark field microscopy for imaging blood cells. *J. Biophotonics* 6, 960-967 (2013).
16. Yakimov, B. P. et al. Label-free characterization of white blood cells using fluorescence lifetime imaging and flow-cytometry: molecular heterogeneity and erythrophagocytosis [Invited]. *Biomed. Opt. Express* 10, (2019).
17. Zeng, Y. et al. Label-free in vivo flow cytometry in zebrafish using two-photon autofluorescence imaging. osapublishing.org.
18. Zeng, Y. et al. Label-free in vivo imaging of human leukocytes using two-photon excited endogenous fluorescence. *J. Biomed. Opt.* 18, 040504 (2013).
19. Li, C. et al. Imaging leukocyte trafficking in vivo with two-photon-excited endogenous tryptophan fluorescence. *Opt. Express* 18, 988 (2010).
20. Wu, C.-H. et al. Imaging Cytometry of Human Leukocytes with Third Harmonic Generation Microscopy OPEN. (2016). doi:10.1038/srep37210
21. Chalut, K. J., Ekpenyong, A. E., Clegg, W. L., Melhuish, I. C. & Guck, J. Quantifying cellular differentiation by physical phenotype using digital holographic microscopy. *Integr. Biol.* (Camb). 4, 280-284 (2012).
22. Ekpenyong, A. E. et al. Bacterial infection of macrophages induces decrease in refractive index. *Journal of Biophotonics* 6, 393-397 (2013).
23. Zangle, T. A., Burnes, D., Mathis, C., Witte, 0. N. & Teitell, M. A. Quantifying Biomass Changes of Single CD8+ T Cells during Antigen Specific Cytotoxicity. *PLoS One* 8, (2013).
24. Zeskind, B. J. et al. Nucleic acid and protein mass mapping by live-cell deep-ultraviolet microscopy. *Nat. Methods* 4,567-569 (2007).
25. Katz, A, Alfan, R. Optical biopsy-detecting cancer with light. *Biomed. Opt. Spectrosc.* (1996).
26. Soltani, S., Ojaghi, A. & Robles, F. E. Deep UV dispersion and absorption spectroscopy of biomolecules. *Biomed. Opt. Express* 10,487 (2019).
27. Zangle, T. A. & Teitell, M. A. Live-cell mass profiling: an emerging approach in quantitative biophysics. *Nat. Methods* 11,1221-1228 (2014).
28. Cheung, M. C., Evans, J. G., McKenna, B. & Ehrlich, D. J. Deep ultraviolet mapping of intracellular protein and nucleic acid in femtograms per pixel. *Cytom. Part A* 79A, 920-932 (2011).
29. Cheung, M. C. et al. Intracellular protein and nucleic acid measured in eight cell types using deep-ultraviolet mass mapping. *Cytom. Part A* 83A, 540-551 (2013).
30. Ojaghi, A., Fay, M. E., Lam, W. A. & Robles, F. E. Ultraviolet Hyperspectral Interferometric Microscopy. *Sci. Rep.* 8,9913 (2018).
31. Byun, H. et al. Optical measurement of biomechanical properties of individual erythrocytes from a sickle cell patient. *Acta Biomater.* 8,4130-4138 (2012).
32. Rodgers, G. P., Dover, G. J., Noguchi, C. T., Schechter, A. N. & Nienhuis, A. W. Hematologic Responses of Patients with Sickle Cell Disease to Treatment with Hydroxyurea. *N. Engl. J. Med.* 322,1037-1045 (1990).
33. Adan, A., Alizada, G., Kiraz, Y., Baran, Y. & Nalbant, A. Flow cytometry: basic principles and applications. *Crit. Rev. Biotechnol.* 37,163-176 (2017).
34. Pettit, E. J. & Hallett, M. B. Localised and global cytosolic Ca2+ changes in neutrophils during engagement of Cd11b/CD18 integrin visualised using confocal laser scanning reconstruction. *J. Cell Sci.* 109 (Pt 7), 1689-94 (1996).
35. Preibisch, S., Saalfeld, S. & Tomancak, P. Globally optimal stitching of tiled 3D microscopic image acquisitions. *Bioinformatics* 25,1463-1465 (2009).
36. Schindelin, J. et al. Fiji: An open-source platform for biological-image analysis. *Nature Methods* 9,676-682 (2012).
37. Zeskind, B. J. et al. Nucleic acid and protein mass mapping by live-cell deep-ultraviolet microscopy. *Nat. Methods* 4, 567-569 (2007).
38. Prahl, S. Optical absorption of hemoglobin. http//oml-c.ogi.edu/spectra/hemoglobin (1999).
39. Cohen, J. A Coefficient of Agreement for Nominal Scales. *Educ. Psychol. Meas.* 20, 37-46 (1960).

What is claimed is:

1. A deep-ultraviolet imaging system comprising:
a broadband light source configured for outputting a light beam comprising ultraviolet wavelengths and non-ultraviolet wavelengths for illuminating a biological sample;
one or more band-pass filters configured for filtering the light beam output from the broadband light source to remove non-ultraviolet wavelengths and to relay ultraviolet wavelengths;
a reception space for reception of a biological sample for illumination by the light beam output from the one or more band-pass filters;
an ultraviolet imaging objective configured for:
collecting light that has interacted with the biological sample; and
relaying the collected light to an image capture device; and
an ultraviolet sensitive image capture device configured for capturing images of the light that is relayed from the ultraviolet imaging objective;
wherein the imaging system is configured to:
capture one or more images of the biological sample at one or more ultraviolet wavelengths; and implement an analysis method on the one or more images to classify or characterize one or more cells in the biological sample.

2. The deep-ultraviolet imaging system according to claim 1, wherein:
the system comprises two or more band-pass filters.

3. The deep-ultraviolet imaging system according to claim 2, wherein:
the two more band-pass filters are supported on a filter stage that is configured for switching between the two or more band-pass filters.

4. The deep-ultraviolet imaging system according to claim 1, wherein:
the one or more band-pass filters are further configured for passing light in a narrow band ultraviolet wavelength of 50 nm or less, each centered around a wavelength in a range of 200-450 nm.

5. The deep-ultraviolet imaging system according to claim 1 further comprising:
a short-pass dichroic mirror for filtering out non-ultraviolet wavelengths from the light beam output from the broadband light source;
wherein the short-pass dichroic mirror is positioned between the broadband light source and the one or more band-pass filters.

6. The deep-ultraviolet imaging system according to claim 1 further comprising:
a parabolic mirror for removing chromatic aberrations and converging the light beam that is output from the broadband light source;
wherein the parabolic mirror is between the broadband light source and the one or more band-pass filters.

7. A deep-ultraviolet imaging system comprising:
a light source comprising a first set of one or more light-emitting diodes (LEDs) for illuminating a biological sample, each LED of the first set configured to output a light beam of narrow band ultraviolet wavelengths of 50 nm or less;
a reception space for reception of a biological sample for illumination by the light beam output from the light source;
an ultraviolet imaging objective configured for:
collecting light that has interacted with the biological sample; and
relaying the collected light to an image capture device; and
an ultraviolet sensitive image capture device configured for capturing images of the light that is relayed from the ultraviolet imaging objective;
wherein the imaging system is configured to:
capture one or more images of the biological sample at one or more ultraviolet wavelengths; and
implement an analysis method on the one or more images to classify or characterize one or more cells in the biological sample.

8. The deep-ultraviolet imaging system according to claim 7, wherein:
the light source two further comprises a second set of one or more LEDs, each LED of the second set configured to output a light beam of narrow band ultraviolet wavelengths of 50 nm or less, each LED of the second set further configured to output ultraviolet wavelengths that differ from ultraviolet wavelengths of each LED of the first set.

9. The deep-ultraviolet imaging system according to claim 7, wherein:
the light source further comprises a second set of one or more LEDs for emitting light in a narrow band ultraviolet wavelength, each centered around a wavelength in a range of 200-400 nm.

10. A deep-ultraviolet imaging system comprising:
a light source configured for outputting a light beam of ultraviolet wavelengths for illuminating a biological sample;
a reception space for reception of a biological sample for illumination by the light beam output from the light source;
an ultraviolet imaging objective adapted to:
collect light that has interacted with the biological sample, which may include absorption and scattering in transmission and back-reflection; and
relay the collected light to an image capture device; and
an ultraviolet sensitive image capture device configured for capturing images of the light that is relayed from the ultraviolet imaging objective;
wherein the imaging system is configured to:
capture one or more images of the biological sample at one or more ultraviolet wavelengths; and
implement an analysis method on the one or more images to classify or characterize one or more cells in the biological sample.

11. A deep-ultraviolet imaging system comprising:
a light source configured for outputting a light beam comprising ultraviolet wavelengths for illuminating a biological sample;
a reception space for reception of a biological sample for illumination by the light beam output from the light source;
an ultraviolet imaging objective configured for:
collecting light that has interacted with the biological sample; and
relaying the collected light to an image capture device; and
an ultraviolet sensitive image capture device configured for capturing images of the light that is relayed from the ultraviolet imaging objective;
wherein the imaging system is configured to:
capture one or more images of the biological sample at one or more ultraviolet wavelengths; and
implement an analysis method on the one or more images to classify or characterize one or more cells in the biological sample; and
wherein the analysis method at least one of:
employs a machine learning algorithm;
identifies and/or phenotypes unique types of cells in the biological sample;
phenotypes blood, bone marrow, and/or tissue in the biological sample; or
comprises transforming the one or more images of the biological sample to one or more corresponding colored images.

12. The deep-ultraviolet imaging system according to claim 11, wherein when the analysis method comprises transforming the one or more images of the biological sample to one or more corresponding colored images, prior to the transforming, the analysis method further comprises normalizing the one or more images using a blank image captured at the one or more ultraviolet wavelengths.

13. The deep-ultraviolet imaging system according to claim 11, wherein when the analysis method comprises transforming the one or more images of the biological sample to one or more corresponding colored images, prior to the transforming, the analysis method further comprises scaling the one or more images with a weight factor and gamma factor, the weight factor and gamma factor for the one or more images being chosen based on the one or more ultraviolet wavelengths.

14. The deep-ultraviolet imaging system according to claim 11, wherein when the analysis method comprises transforming the one or more images of the biological sample to one or more corresponding colored images, the transforming comprises assigning the one or more images to a channel in the red, green, and blue (RGB) color-space based on the one or more ultraviolet wavelengths.

15. The deep-ultraviolet imaging system according to claim 11, wherein when the analysis method comprises transforming the one or more images of the biological sample to one or more corresponding colored images, the transforming is performed such that colors in the one or more corresponding colored images distinguish molecular and structural entities in the image.

16. A method of characterizing or classifying cells in a biological sample comprising:
    illuminating the biological sample with light comprising a narrow band of ultraviolet wavelengths having a bandwidth of 50 nm or less and centered on a wavelength of 255-260 nm;
    capturing one or more images of the biological sample at the one or more narrow band of ultraviolet wavelengths; and
    analyzing the captured one or more images to classify or characterize one or more cells in the biological sample.

* * * * *